(12) United States Patent
Valentine et al.

(10) Patent No.: US 6,296,868 B1
(45) Date of Patent: Oct. 2, 2001

(54) CHEWABLE TABLETS CONTAINING MANNITOL AND ASPARTAME

(75) Inventors: William Valentine; William K. Valentine, both of Lawrenceville, GA (US)

(73) Assignee: Advanced Technology Pharmaceuticals Corporation, Dacula, GA (US)

( * ) Notice: Subject to any disclaimer, the term of this patent is extended or adjusted under 35 U.S.C. 154(b) by 0 days.

(21) Appl. No.: 09/195,811

(22) Filed: Nov. 19, 1998

(51) Int. Cl.[7] .............................. A61K 9/16; A61K 9/20
(52) U.S. Cl. .................. 424/441; 424/464; 424/465; 424/489; 424/499; 427/2.15
(58) Field of Search .................. 424/441, 464, 424/465, 489, 499; 427/2.14, 2.15; 426/548

(56) References Cited

U.S. PATENT DOCUMENTS

| | | | |
|---|---|---|---|
| 4,684,534 | * | 8/1987 | Valentine .............................. 424/441 |
| 5,077,053 | * | 12/1991 | Kuncewitch et al. ................ 424/441 |
| 5,084,278 | | 1/1992 | Mehta . |
| 5,188,825 | | 2/1993 | Iles et al. . |
| 5,206,025 | | 4/1993 | Courteille et al. . |
| 5,244,670 | | 9/1993 | Upson et al. . |
| 5,275,822 | | 1/1994 | Valentine et al. . |
| 5,284,659 | | 2/1994 | Cherukuri et al. . |
| 5,286,489 | | 2/1994 | Tsau et al. . |
| 5,298,261 | | 3/1994 | Pebley et al. . |
| 5,320,855 | | 6/1994 | Roche et al. . |
| 5,330,763 | | 7/1994 | Gole et al. . |
| 5,385,749 | * | 1/1995 | Serpelloni et al. ................ 426/658 |
| 5,401,514 | | 3/1995 | Juch et al. . |
| 5,573,777 | * | 11/1996 | Serpelloni et al. ................ 424/440 |
| 5,679,398 | * | 10/1997 | Serpelloni et al. ................ 426/658 |
| 5,711,961 | * | 1/1998 | Reiner et al. ......................... 424/441 |
| 5,753,255 | * | 5/1998 | Chavkin et al. ..................... 424/441 |
| 5,837,277 | * | 11/1998 | Hayward .............................. 424/441 |
| 5,917,081 | * | 6/1999 | Seyffert et al. .......................... 560/8 |
| 5,939,091 | * | 8/1999 | Eoga et al. ........................... 424/441 |
| 5,962,022 | * | 10/1999 | Bolt et al. ............................ 424/466 |
| 5,965,162 | * | 10/1999 | Fuisz et al. .......................... 424/464 |

OTHER PUBLICATIONS

Ullmann's Encyclopedia of Industrial Chemistry. 5th, Completely Revised Edition, vol. B2: Unit Operations I, Particle Technology: Size Enlargement. pp. 7–1 to 7–4. (1988).*

* cited by examiner

Primary Examiner—Robert H. Harrison
(74) Attorney, Agent, or Firm—DeLio & Peterson, LLC

(57) ABSTRACT

Chewable tablets and particulate food and pharmaceutical products are disclosed which are made from agglomerates comprising an alcohol sugar such as mannitol and a high intensity sweetener such as Aspartame from which agglomerate tablets may be directly compressed, and processes for making the agglomerates and tablets. The tablets or particulate product containing the agglomerate may contain active ingredients blended with the agglomerate or as part of the agglomerate structure. Tablets and particulate products according to the invention can contain active ingredients such as pharmaceuticals (e.g., antacids, analgesics, cough medicine, drugs, etc.) breath sweeteners, vitamins and dietary supplements, to name a few. The high intensity sweetener containing agglomerates can also be used to make solid food mix type products such as sugar free ice tea mixes.

16 Claims, No Drawings

CHEWABLE TABLETS CONTAINING MANNITOL AND ASPARTAME

BACKGROUND OF THE INVENTION

1. Field of the Invention

The present invention relates generally to alcohol sugar high intensity sweetener agglomerate compositions which are useful in food and pharmaceutical products because of their flowability, compressibility, mixability, stability and dissolution characteristics, among others and, in particular, to agglomerates of an alcohol sugar preferably mannitol and a high intensity sweetener preferably Aspartame which agglomerates are made using a fluid bed process and are used to make chewable tablets and particulate products requiring a high intensity sweetener, and to processes for making the co-agglomerates, tablets and particulate products.

2. Description of Related Art

A need has long existed in the food and pharmaceutical industry for high intensity sweetener containing products in a solid form which store well, are convenient Sand pleasant to take, efficacious, fast acting and storage stable. For example, a particulate product such as a sugar free ice tea mix requires that the product be free flowing and the high intensity sweetener stable to ingredients in the mix such as acidulents like citric acid. A high intensity sweetener is also used for a masking purpose to-mask the bad taste of active ingredients in a product such as a chewable tablet containing acetaminophen. Additionally, solid swallowable antacid tablets are not particularly good tasting and do not sweeten the breath, which would be extremely desirable characteristics of a chewable tablet product for those who suffer from esophagal reflux or sour breath.

High intensity sweeteners such as Aspartame unfortunately are not easily formulated in food and pharmaceutical products and this presents a formidable problem in the food and drug industries. Aspartame, for example, contains groups such as dipeptide linkages which are unstable when mixed with acidulents such as citric acid or an alkatine antacid material such as magnesium hydroxide. The breaking of the dipeptide link results in a loss of sweetness. Aspartame also enters into Maillard type "browning" reactions when mixed with a reducing sugar such as dextrose. Dissolution of the high intensity sweetener is also a problem because they generally evidence slow and undesirable dissolution in water, e.g., the sweetener floats on the surface of the water and slowly dissolves or the sweetener sinks to the bottom of the water and slowly dissolves. High intensity sweeteners typically are commercially available as fine powders which have a high degree of discernible static charge which makes homogenous mixing of the formulation difficult. Poor compressibility of high intensity sweeteners is an additional problem for formulators.

Bearing in mind the problems and deficiencies of the prior art, it is therefore an object of the present invention to provide a high intensity sweetener agglomerate composition which is stable, free flowing, compressible, mixable and has rapid dissolution properties and which is capable of being used in a variety of solid food and pharmaceutical products such as food and drink mixes and chewable tablets.

It is another object of the present invention to provide a tablet containing a high intensity sweetener which stores well and liquefies quickly in the mouth upon chewing and is pleasant tasting.

It is another object of the present invention to provide a tablet containing a high intensity sweetener which is made by direct compression and which tablet includes a substantial quantity of the sweetener which in its raw material form is a powder that can not be easily compacted into a cohesive tablet.

It is a further object of the invention to provide process for making high intensity sweetener containing agglomerates which can be used to make particulate and tablet food and pharmaceutical products.

Other objects and advantages of the invention will be readily apparent from the following description.

SUMMARY OF The INVENTION

The above and other objects and advantages, which will be apparent to those skilled in the art, are achieved in the present invention which is directed to, in a broad aspect, an agglomerate sweetener composition comprising an alcohol sugar such as mannitol and a high intensity sweetener. The agglomerate typically has a porous, high surface area void-like structure and is preferably made using a fluidized bed process. The agglomerates preferably comprise mannitol as the alcohol sugar and Aspartame as the high intensity sweetener. A water soluble binder is used to form the agglomerate and is selected from the group consisting of an alcohol sugar which can be the same as the alcohol sugar forming the base of the composition, a water soluble carbohydrate, maltodextrin, polyvinylpyrrolidone and carboxy methyl cellulose (CMC) among others. The preferred binders are the same alcohol sugar forming the base and maltodextrin.

The quantity of water-soluble binder is an effective amount needed to form the agglomerate and is in the range of up to about 10 percent by weight of the agglomerate, (including the high intensity sweetener), and preferably from about 1 percent to about 5 percent. The alcohol sugar particles comprise about 80 percent to about 97 percent and the high intensity sweetener about 1 percent to 10 percent by weight of the agglomerate (including the high intensity sweetener). The ranges vary depending on the product in which the agglomerate is to be used. The particle size of the materials used to make the agglomerates and the particulate size of the agglomerates may likewise vary widely as described below.

A tablet made according to the present invention is directly compressed from the high surface area porous alcohol sugar based high intensity sweetener agglomerate particles preferably using a relatively low tabletting pressure to form a relatively soft, quick-liquefying interior and a relatively hard, protective outer shell which resists liquefaction even though it is formed from the same agglomerate particles which form the tablet interior. At least some of the ingredients of the agglomerate particles jn the interior of the tablet quickly dissolve or partially dissolve when the tablet is broken into pieces and contacted with small amounts of a liquid, particularly water and/or saliva, as during mastication for example, and any remaining ingredients which do not dissolve in the liquid become dispersed in the liquid and dissolved ingredients, so that the resulting liquid is smooth and essentially without perceivable grit. The relatively hard outer shell resists liquefaction until it is broken, for example, by chewing. Accordingly, the overall preferred chewable tablet structure is such that the tablet is storage stable and easily portable, thereby providing a unit dose in a most convenient form, but is also readily liquefied and melts in the saliva of the mouth during mastication without requiring water or some other liquid, so that the tablet provides all of the benefits normally associated only with liquid dosage forms.

Quick-liquifying, chewable tablets are shown in U.S. Pat. No. 4,684,534, which patent is incorporated herein by reference and which patent is assigned to the assignee of the present invention. The patent discloses carbohydrate-based agglomerates, a method for making the agglomerates and tablets made from the agglomerate.

The storage stable high intensity sweetener containing agglomerate comprises an alcohol sugar, high intensity sweetener and a water-soluble binder. The agglomerate may be used in food products without an active ingredient. Typically the agglomerate is used with an active ingredient such as in an ice tea mix or an antacid tablet. The agglomerate is preferably blended with an active ingredient in the formulation. The active ingredient and agglomerate can also be mixed together to;cause the active ingredient to be entrained by and dispersed in the agglomerate. This agglomerate can then be added to the product formulation. The active ingredient can also be formed as part of the agglomerate during the agglomeration process. The high intensity sweetener can be absorbed onto a water-soluble agglomerate but this method and agglomerate composition are not preferred.

The agglomerate as formed has a bulk density which is relatively low compared to the alcohol sugar base and high intensity sweetener which are used to make the agglomerate and is typically in the range of about 0.35 gm/cc to about 0.55 gm/cc. A substantial part of the agglomerate consists of voids, i.e., pores or ducts, which provide an extremely large surface area capable of entraining and dispersing substantial quantities of active ingredients ordinarily about 10 percent to about 50 percent by weight of the finished agglomerate (which includes the entrained active ingredient). The agglomerate has particular utility as a direct compression agglomerate from which tablets according to the invention can be made particularly chewable tablets which liquify in saliva.

A preferred process for making the alcohol sugar and high intensity sweetener agglomerate comprises the steps of forming a fluidized bed of the alcohol sugar and high intensity sweetener particles, intermittently spraying a solution of the water soluble binder in a droplet size into the fluidized bed so as to cause intimate commingling of solution, alcohol sugar and high intensity sweetener particles and adhesion together of alcohol sugar particles and high intensity sweetener particles to form agglomerated particles, drying the particles in the fluidized bed between intermittent sprayings, and continuing spraying and drying until the desired amount of binder solution has been sprayed into the bed. Thereafter, the agglomerated particles are dried to a desired moisture content or the equilibrium moisture content. The amount of liquid binder solution sprayed corresponds to a binder content in the agglomerate of from about 1 percent to about 10 percent by weight to the agglomerate. The alcohol sugar and high intensity sweetener agglomerate and active ingredient and other ingredients such as lubricants, flavors, etc. are mixed, preferably in a low shear blender, to form a blend for tabletting by direct compression or for use as a flowable food or pharmaceutical product.

The agglomerate composition can also be made using a granulating procedure whereby the alcohol sugar, high intensity sweetener and binder are mixed together to form a paste like material, screened, dried and sized.

The agglomerate can, as formed, be used to entrain the active ingredient and other materials such as a lubricant and flavors in the formulation to be made into a product. In addition, an agglomerate containing the active ingredient as part of the agglomerate structure can be formed by the process described above for the agglomerate formed without an active ingredient, except that the active ingredient is mixed with the alcohol sugar and high intensity sweetener particles and a fluidized bed is formed of this mixture. The active ingredient and/or high intensity sweetener may also be added with the binder. Agglomerates formed with an active ingredient have a porous structure similar to that of agglomerates formed without an active ingredient.

The preferred method to form the agglomerate is by a fluidized bed process wherein the alcohol sugar and high intensity sweetener are fluidized and a binder solution sprayed onto the fluidized bed.

It is preferred that the alcohol sugar particles used to make the agglomerate pass about 50 mesh (particle size less than about 300 microns). The high intensity sweetener typically passes about 300 mesh (particle size less than about 50 microns). Mesh sizes given therein refer to the U.S. Standard Sieve Series. The final particle size of the agglomerate is preferably greater than about 80 mesh (111 microns).

A process for making a tablet from the alcohol sugar-high intensity sweetener agglomerates described above, typically including about 0.4 percent to about 1 percent of a lubricant, comprises compressing the agglomerate particles which were mixed with any active ingredient, flavors, etc., in a conventional tablet-forming apparatus to a hardness sufficient to hold the tablet together and preferably substantially destroy the open pore structure of the agglomerate at the surface of the tablet while substantially maintaining the open pore, i.e., large surface area, structure of the agglomerate in the interior of the tablet. Thus, the agglomerate is compressed so that the interior of the tablet preferably retains the essential porous structure and other physical characteristics of the agglomerate which enable it to liquify quickly, while the physical characteristics of the agglomerate are changed primarily at the surface of the tablet.

For the materials described herein, it has been found that the tablets are preferably compressed to a hardness generally about 3 kp to about 8 kp or higher, preferably about 6 kp, which compression forms an interior which essentially retains the physical structure of the agglomerate. A thinner outer shell is preferred since more force is required to break a tablet with a thicker shell and less material is provided in the interior of a tablet having a thicker shell. Since the thickness of the outer shell has been found to increase with tablet hardness, a preferred range for compression of the agglomerate is a hardness of about 3 kp to about 6 kp.

Pressures applied to compress the agglomerates into tablets having a hardness of about 3 kp to 6 kp were found to be in the order of about one-third the pressures ordinarily used to make tablets.

The term "high intensity sweetener" is used herein in a broad sense and encompasses any high intensity sweetener material which can be formed into an agglomerate or entrained in an agglomerate. The preferred high intensity sweetener is Aspartame but other high intensity sweeteners such as Acesulfame, Alatame, Steviasides, saccharin, cyclamates, etc., may also be employed to make the agglomerate high intensity sweetener composition of the invention. The term "active ingredient" is used herein in a broad sense and means a pharmaceutical such as an arntacid, analgesic or drug; or a flavor, breath sweetener, vitamin, dietary supplement, or nutrient; or the like and combinations thereof. Active ingredients include but are not limited to food acids; insoluble metal and mineral hydroxides, carbonates, oxides, polycarbophils and salts thereof; adsorbates of active drugs on a magnesium trisilicate base and on a magnesium aluminum silicate base.

DESCRIPTION OF THE PREFERRED EMBODIMENTS

The invention is broadly applicable to making a wide variety of food and pharmaceutical products including particulate blends and chewable tablets including but not limited to, sugar free iced tea mixes, and sugar free antacid tablets, cough medicine tablets, sore throat tablets, breath freshener tablets, vitamin tablets, calcium tablets, dietary supplement and nutrient tablets, laxative tablets, cold tablets, analgesic tablets, anti-diarrhea tablets, reducing tablets, pain reliever tablets, sleeping tablets, and many prescription and non-prescription drug and pharmaceutical tablets.

Mannitol is the preferred alcohol sugar and the following will be directed to mannitol for convenience. Other alcohol sugars include sorbitol and xylitol.

Agglomerates according to the invention are preferably formed by a fluidized bed/agglomeration process in which the particles to be agglomerated are maintained in a gaseous suspension and a binder in a fine spray is applied to the suspended particles to cause them to adhere together and build into agglomerated particles having the open pore, large surface area structure described herein. The suspended alcohol sugar particles from which the agglomerates are made preferably pass 50 mesh, while the high intensity sweetener and ingredients are typically fine powders, for example, passing 300 mesh.

The binder may be used alone in solution and/or with the high intensity sweetener and/or active ingredient. Preferably, the binder is used to make a binder solution and the alcohol sugar and high intensity sweetener make up the fluidized bed. The active ingredient in the final formulation is preferably added by blending with the agglomerate. The binder is typically applied in a mist-like or atomized spray having a droplet size of preferably from about 20 microns to about 100 microns in diameter. The spray is preferably applied intermittently and the bed particles are dried between sprayings while they are continuously maintained suspended and in a fluidized state. Intermittent spray and drying continues until the required amount of binder solution has been sprayed into the bed. The moisture content of the bed is thereafter reduced preferably directly to the final desired moisture content or the equilibrium moisture content, and the agglomerated particles are removed from the bed and sized.

A spray granulator suitable for making agglomerates of the invention is a Freund Model FL80 pilot-production Flow-Coater. A schematic diagram of the Freund Model FL80 Flow-Coater is depicted in FIGS. 1 and 2 of U.S. Pat. No. 4,684,534, supra.

It is preferred that air be used as the gas for atomizing the binder solution ("atomizing air"), as the gas for controlling the pattern of the spray ("spray pattern air"), and as the gas for suspending and fluidizing the particles in the body of the fluidized flow coater. Other suitable gases may likewise be employed.

The air pressure of the atomizing air and pattern air and the pumping rate of the liquid binder solution are set and controlled in accordance with the particular agglomerate being produced as is well-known in the art. Also controlled are the quantity of fluidizing air being drawn to fluidize the bed particles, and the heat exchangers to set the temperature of the air introduced into the flow coater.

For the materials disclosed herein and similar materials, the atomizing air pressure and the pattern air pressure is typically in the general range of about 1.5 atm to about 6 atm, the atomizing air flow in the general range of about $100L^3$/hr to about $200L^3$/hr, the pattern air flow in the general range of about $10L^3$/hr to about $40L^3$/hr, and the liquid binder flow rate in the general range of about 60 ml/min to about 1,200 ml/min. The following are preferred: atomizing air pressure and pattern air pressure, 4 atm; atomizing air flow, $120L^3$/hr: pattern air flow, $20L^3$/hr; liquid binder flow rate 250 ml/min; air pressure within the flow coater, 1 atm; fluidizing air temperature about 60–80° C.

The different process parameters described above can be set and individually controlled by visual observation and manual setting, or by control systems which semi-automatically or automatically sense and regulate the parameters in accordance with a given control sequence. Process parameters for a particular agglomerate can be programmed into or manually set in to such control system. Computerized control systems can be used, if desired, and the construction and operation of control systems for controlling the foregoing process are within the skill of those in the computer and control system arts.

Apparatus other than the Freund FL 80 Flow-Coater can be used to produce agglomerates according to the invention. One such apparatus commercially available is a Freund Mini-Flow Coater. This particular apparatus includes a single, centrally-disposed nozzle which sprays atomized binder solution into a fluidized bed from above the bed.

Agglomerates as shown in the examples below, were made in accordance with the process described above using a Freund Model FL 80 Flow-Coater or a Freund Mini-Flow-Coater. The agglomerates were made from materials as indicated below. The maltodextrin binder materials typically have a DE of less than about 20 and preferably in the range of about 5 to about 12.

The alcohol sugar particles passed 50 mesh (particle size less than about 300 microns), and the high intensity sweetener and water-insoluble active ingredients passed 325 mesh (particle size less than about 44 microns). Lubricant particles passed 325 mesh and other materials such as flavors passed 100 mesh. The precise size of the alcohol sugar particles is not critical, but agglomerates made from materials having sizes larger than about 50 mesh for the alcohol sugar particles and larger than about 300 mesh for the active ingredient generally do not typically produce tablets which liquify and melt in the mouth as quickly and as completely as those made with smaller particles. Active ingredients which do not dissolve in the liquid in which a tablet made from the agglomerate is to liquify, e.g., water or saliva, preferably have a particle size of less than about 10 microns. A preferred particle size for such active ingredients is from about 3 microns to about 10 microns.

Before being compressed into tablets, the agglomerate particles are preferably sized preferably between −22 mesh to +100 mesh (between about 150 microns and about 800 microns). The agglomerate particle size is also not critical and particles in the above range produce tablets and flowable particulate products having preferred characteristics.

Agglomerates made in accordance with the invention have a honeycomb or zeolite-like structure as described above, in which there are large amounts of voids and surface area.

Tablets made in accordance with the invention were found to be hard and smooth on the outside but rough, granular and soft on the inside, normally resistant to moisture on the outside and liquid-reactive on the inside. When masticated, the tablets liquefied without perceivable grit within about 20 seconds.

Specific examples of agglomerates and tablets made from the agglomerates in accordance with the invention follow. Such Examples are intended to be exemplary and not to be exhaustive or limiting.

In all of the examples which include maltodextrin, the maltodextrin was Maltrin M-100 (−100 mesh).

EXAMPLES

The following examples will serve to further illustrate the components and details of preparation for the mannitol based spray granulated co-agglomerate combinates of this invention.

Example #1

A bench model Freund Mini Flow-Coater fluid bed agglomerator product bowl was charged with:

| Mannitol USP (fine powder) | 435.0 g |
|---|---|

The bed was fluidized and pre-heated for a period of 5 minutes.

An agglomerating pump solution was prepared as follows:

| Mannitol USP | 15.0 g |
|---|---|
| water | 135.0 g |

The mannitol water solution was heated to 45° C. and stirred until clear.

The preheated bed was energized with inlet air at a temperature of 70° C. and the pump solution was delivered at a rate of 3 ml/minute with an atomizing air pressure of 1.0 ATM.

The pump solution was delivered intermittently in 1 minute cycles, followed by air purging of the filter and cycles were continued until all of the mannitol solution was delivered. The product was then dried to a loss on drying (LOD) moisture content of less than 0.5%. The finished dust-free agglomerated product dissolved well in water and when mixed with 1.0% by weight magnesium stearate pressed into satisfactory non-sweet chewable tablets.

Example #2

A bench model Freund Mini Flow-Coater fluid bed agglomerator product owl was charged with:

| Mannitol USP | 450 g |
|---|---|

The bed was fluidized and preheated for a period of 5 minutes.

An agglomerating pump solution was prepared as follows:

| 10 DE Maltodextrin | 15 g |
|---|---|
| water | 135 g | the 10 DE maltodextrin solution was heated to 35° C. and stirred until clear.

The pre-heated bed was energized with inlet air at a temperature of 70° C. and the pump solution was delivered intermittently at a rate of 3ml/min in 1 minute cycles, followed by air purging of the filter and the cycles were continued until all of the maltodextrin pump solution was delivered. The product was dried to a (LOD) moisture content of less than 1%.

The finished dust-free agglomerated product dissolved well in water and when mixed with 1% by weight magnesium stearate pressed into satisfactory non-sweet chewable tablets.

Example #3

A bench model Freund Mini Flow-Coater fluid bed agglomerator product bowl was charged with:

| Mannitol USP | 430.5 g |
|---|---|
| Aspartame | 4.5 g |

The bed was energized and fluidized for a period of 5 minutes.

An agglomerating pump solution was prepared as follows:

| Mannitol | 15.0 g |
|---|---|
| water | 135.0 g |

The bed was energized with inlet air at a temperature of 70° C. and the pump solution was delivered at a rate of 3 ml/minute with atomizing air pressure at 1 ATM. The pump solution was delivered intermittently in 1 minute cycles, followed by air purging of the filter, and the cycles were continued until all of the mannitol pump solution was delivered. The product was then dried to a loss on drying (LOD) moisture content of less than 0.5%.

The finished dust-free agglomerated product dissolved well in water and when mixed with 1% by weight magnesium stearate pressed into commercially satisfactory sweet chewable tablets.

Example #4

A bench model mini flo-coater fluid bed agglomerator product bowl was charged with:

| Mannitol | 430.5 |
|---|---|
| Aspartame | 4.5 |

The bed was energized to effect fluidization and mixed for a period of 5 minutes.

An agglomerating pump solution was prepared as follows:

| | |
|---|---|
| Maltodextrin (10 DE) | 15 g |
| water | 135 g |

The maltodextrin water solution was heated to 35° C. and stirred until clear. The system was energized and the fluidized bed agglomerated as in example 3.

The finished dust-free agglomerated product dissolved well in water and when mixed with 1% by weight magnesium stearate pressed into commercially satisfactory sweet chewable tablets.

Example #5

A bench model Freund Mini Flow-Coater fluid bed agglomerator product bowl was charged with:

| | |
|---|---|
| Mannitol | 430.5 |

The bed was energized and preheated for a period of 5 minutes. An agglomerating pump solution was prepared as follows:

| | |
|---|---|
| Maltodextrin 10 DE | 15.0 g |
| Aspartame | 4.5 g |
| water | 135.0 g |

The maltodextrin Aspartame solution was heated to 35° C. and stirred until clear. The system was energized and the fluidized bed agglomerated as in Example #3.

The finished dust-free agglomerated product dissolved well in water and when mixed with 1% by weight magnesium stearate pressed into commercially satisfactory sweet chewable tablets.

Example #6

A bench model Freund Mini-Flow-Coater fluid bed agglomerator product bowl was charged with:

| | |
|---|---|
| Mannitol USP | 430.5 g |

The bed was fluidized and preheated for a period of 5 minutes.

An agglomerating pump solution was prepared as follows:

| | |
|---|---|
| Mannitol | 15.0 g |
| Aspartame | 4.5 g |
| water | 135.0 g |

The mannitol Aspartame solution was heated to 35° C. and stirred until clear. The system was energized and the fluidized bed agglomerated as in Example #3.

The finished dust free agglomerated product dissolved well in water and when mixed with 1% magnesium stearate pressed well into satisfactory sweet chewable tablets.

Example #7

A bench model mini flo-coater fluid bed agglomerator product bowl was charged with pre-mixed and milled:

| | |
|---|---|
| Mannitol | 407.70 g |
| Aspartame | 4.95 g |
| corn starch | 22.50 g |

The bed was fluidized and preheated for a period of 5 minutes.

An agglomerating pump solution was prepared as follows:

| | |
|---|---|
| Maltodextrin | 13.5 g |
| Sodium chloride | 1.35 g |
| water | 135.0 |

The maltodextrin 10 D.E., sodium chloride and water were heated to 35° C. and stirred until clear. The system was energized and the fluidized bed agglomerated as in example 3.

The finished dust-free agglomerated product was mixed with 1% magnesium stearate, 3.5% anhydrous citric acid, and 3.5% sodium bicarbonate. The free flowing dust-free tablet base compressed readily to form sweet, mildly effervescent, rapidly dissolving chewable tablets. The tablets maintained their level of effervescence after storage in glass bottles and held at 37° C. or 45° C. for a period of 30 days.

Example #8

A Freund model FL-80 product bowl was charged with the following materials:

| | |
|---|---|
| Mannitol USP + | 52.48 kg |
| A premixed and co-milled blend of Mannitol 10.00 kg, Aspartame 0.71, corn starch 3.50 kg | 14.21 kg |

The loaded product bowl was lifted into position and secured to seal the agglomerating chamber.

An agglomerating pump solution was prepared as follows:

| | |
|---|---|
| Maltodextrin 10 DE | 3.10 kg |
| Sodium chloride | 0.21 |
| 3% hydrogen peroxide | 0.25 kg |
| water | 14.00 kg |

The mix was charged into an agitated holding tank, heated to 85° C. and mixed until clear.

The following operational parameters for the agglomeration of the fluidized bed were set into the operational computer prior to energizing the machine:

| | |
|---|---|
| Inlet air temperature | 70° C. |
| Atomizing air pressure | 4 ATM |
| Pump delivery rate | 0.425 L/min. |
| pump cycle | 1.0 min. |
| Mechanical Filter Shake | 15 sec. |

-continued

| # of pump shake cycles | 47 |
|---|---|
| Atomizing air to spray guns | 170 L/Hr |
| Pattern air to spray guns | 20 L/Hr |
| Bed mixing time | 5 min. |

With the established parameters entered into the electronic control system of the FL-80, the machine was energized and fluidization of the bed was effected.

After each minute of time in the mix cycle, fluidization was interrupted and the filters were automatically shaken followed by re-established fluidization. Following the mix cycle, atomized agglomerating solution was delivered onto the bed for 1 minute. Fluidization of the bed was interrupted and followed by filter shaking to return unagglomerated material to the bed. The spray shake cycles continued until all of the pump atomizing solution plus the system flush water was delivered to the bed.

The bed was then dried by fluidization in the 70° C. inlet air with the same intermittent shaking cycle interval as in the mixing mode. The final product was removed at a moisture level of less than 1% LOD as determined via Computrac moisture analysis.

The finished dust-free product demonstrated rapid flow rate and, with 1% by weight magnesium stearate added, ease of compression into sweet chewable tablets.

Example #9

A Freund model FL-80 product bowl was charged with the following materials:

| Mannitol USP + | 52.37 kg |
|---|---|
| A pre-mixed and co-milled blend of Mannitol 10 kg, Aspartame 1.82 kg and corn starch 3.5 kg | 15.32 kg |

The loaded product bowl was lifted into position and secured to seal the agglomerating chamber.

An agglomerating pump solution was prepared as follows:

| Maltodextrin 10 DE | 3.10 kg |
|---|---|
| Sodium Chloride | 0.21 kg |
| 3% Hydrogen peroxide | 0.25 kg |
| water | 14.00 kg |

The materials were charged into a steam jacketed, agitated holding tank, heated to 85° C. and mixed until clear.

The agglomeration of the bed was accomplished in the same manner as in Example #7 and the same results were obtained.

Example #10

A Freund model FL-80 product bowl was charged with the following materials:

| Mannitol USP + | 49.44 kg |
|---|---|
| A pre-mixed and co-milled blend of Mannitol 10 kg Aspartame 3.75 kg and corn starch 3.5 kg was added | 17.25 kg |

The loaded product was lifted into position and secured in order to seal the agglomerating chamber.

An agglomerating pump solution was prepared as follows:

| Maltodextrin 10 DE | 3.10 kg |
|---|---|
| Sodium chloride | 0.21 kg |
| 3% Hydrogen peroxide | 0.25 kg |
| water | 10.00 kg |

The materials were charged into a steam jacketed, agitated, holding tank, heated to 85° C. and stirred until clear.

The agglomeration of the bed was accomplished in the same manner as in Example #7 and the same results were obtained.

Analysis of Examples #8, #9 and #10 revealed that the lots were microbiologically acceptable and that each lot contained the proper validated quantity of Aspartame.

| Example #8 | Sweet Mannitol with 1% Aspartame |
|---|---|
| Example #9 | Sweet Mannitol with 2.5% Aspartame |
| Example #10 | Sweet Mannitol with 5% Aspartame |

Example #11

The following formulation was prepared utilizing "Sweet Mannitol with 1% Aspartame Agglomerates" (Example #8):

| 1% Sweet mannitol agglomerates | 75.0% w/w |
|---|---|
| Coated pseudoephedrine HCl (19%) | 7.9 |
| Coated chlorpheniramine maleate (10%) | 1.0 |
| Tastemasker | 4.0 |
| Sodium bicarbonate (−80 mesh) | 4.0 |
| Citric acid anhydrous (−80 mesh) | 4.0 |
| Flavors | 2.6 |
| Magnesium stearate | 1.1 |
| Silicon dioxide | 0.4 |

The tablet ingredients were mixed with the agglomerated 1% sweet mannitol and compressed. The tablet blend had a high rate of flow and satisfactorily compressed into ⁹⁄₁₆" flat faced beveled edged tablets at a rate of 2000 tablets/minute. Tablets were ejected at a hardness of 4 kP, and had a friability of less than 0.5%.

When placed in) the mouth and chewed, the tablets were satisfactorily liquescent (i.e. dissolved/disintegrated and swallowed within 20 seconds). Following storage at 37° C. for a period of 1 year, the tablets evidenced satisfactory chemical and physical stability with respect to liquescense rate, effervescent rate, active ingredient content, sodium, sodium bicarbonate content, Aspartame content, taste, active ingredient content, color, flavor and hardness.

Example #12

The following formulation was prepared utilizing "Sweet Mannitol with 1% Aspartame Agglomerates" (Example #8)

and "Sweet Mannitol with 2.5% Aspartame Agglomerates" (Example #9).

| Sweet mannitol agglomerates 1% | 45.748% w/w |
|---|---|
| Sweet mannitol agglomerates 2.5% | 7.000 |
| Coated pseudoephedrine HCl (19%) | 7.900 |
| Dextromethorphan HBr Adsorbate (10%) | 5.000 |
| Tastemasker | 4.000 |
| Citric acid anhydrous (−80 mesh) | 4.000 |
| Sodium bicarbonate | 4.000 |
| Flavor | 2.600 |
| Magnesium stearate | 1.100 |
| Coated Acetaminophen (93%) | 17.2 |
| Coated chlorpheniramine maleate (10%) | 1.000 |
| Silicon dioxide | 0.400 |
| Lake color | 0.052 |

The tablet ingredients were mixed with the agglomerated sweet mannitol and compressed. The tablet blend had a high rate of flow and satisfactorily compressed into 9/16 flat faced beveled edged 1000 mg tablets at a sustained rate of 2000 tablets/minute. The ejected tablets had a hardness of 4 kP and a friability value of less than 0.5%.

When placed in the mouth and chewed, the tablets were satisfactorily liquescent (i.e., dissolved/disintegrated and swallowed within 20 seconds). Following storage at 37° C. for a period of one year, the tablets evidenced satisfactory chemical and physical stability with respect to liquescense rate, effervescence rate, active ingredient content, sodium bicarbonate content, Aspartame content, color, flavor and hardness.

Example #13

The following formulation was prepared utilizing "Sweet Mannitol with 2.5% Aspartame Agglomerates" (Example #9):

| Sweet mannitol agglomerates 2.5% | 50.7% w/w |
|---|---|
| Coated Acetaminophen | 17.2 |
| Coated pseudoephedrine HCl (19%) | 7.9 |
| Dextromethorphan HBr Adsorbate (10%) | 5.0 |
| Flavors | 5.1 |
| Tastemasker | 4.0 |
| Citric acid anhydrous (−80 mesh) | 4.0 |
| Sodium bicarbonate (−80 mesh) | 4.0 |
| Magnesium stearate | 1.1 |
| Lake color blend | 0.6 |
| Silicon dioxide | 0.4 |

The tablet ingredients were mixed with the Sweet Mannitol with 2.5% Agglomerates and compressed. The tablet blend had a high rate of flow and successfully compressed on 9/16 flat faced beveled edged punches at a weight of 1000 mg/tablet at a sustained rate of 2000 tablets/minute. The ejected tablets had a hardness of 4kP and a friability value of less than 0.5%.

When placed in the mouth and chewed, the tablets were satisfactorily liquescent (i.e., dissolved/disintegrated and swallowed within 20 seconds). Following storage at 37° C. for a period of one year, the tablets evidenced satisfactory chemical and physical stability with respect to liquescense rate, effervescent rate, active ingredient content, sodium bicarbonate content, Aspartame content, color, flavor and hardness.

Example #14

The following formulation was prepared utilizing "Sweet Mannitol with 5% Aspartame Agglomerates" (Example #10):

| Sweet mannitol agglomerates 5.0% | 64.5% w/w |
|---|---|
| Coated Acetaminophen (93%) | 18.0 |
| Tastemasker | 4.0 |
| Citric acid anhydrous (−80 mesh) | 4.0 |
| Sodium bicarbonate (−80 mesh) | 4.0 |
| Magnesium Trisilicate | 4.0 |
| Magnesium stearate | 1.1 |
| Flavors | 0.4 |

The tablet ingredients were mixed with the Sweet Mannitol with 5% Aspartame Agglomerates and compressed. The tablet blend had a high rate of flow and chewable tablets were compressed at a weight of 1950 mg on ¾" standard concave punches at a satisfactory sustained rate of speed. The ejected tablets had a hardness of 4–5 kP and a friability value of less than 1%.

When placed in the mouth and chewed, the tablets were satisfactorily liquescent (i.e, dissolved/disintegrated and swallowed within 20 seconds). Following storage stability for a period of 4 months at 37° C., the tablets evidenced satisfactory stability with respect to liquescense rate, effervescence rate, active ingredient content, sodium bicarbonate content, Aspartame content, color, flavor and hardness.

Example #15

To show the stability of a high intensity sweetener such as Aspartame in a tablet made using the preferred alcohol sugar agglomerates of the invention, dextrose mono-hydrate and mannitol agglomerates were prepared by a fluidized process as described above and the agglomerates admixed with Aspartame and other ingredients as indicated below in the Table to form comparative tablets. Color change is an indicator of chemical degradation of the Aspartame via a color changing Maillard reaction. The stability results in months (m) at a specified temperature are also indicated below in the Table.

TABLE

| | | Stability | | | | | |
|---|---|---|---|---|---|---|---|
| Tablet | Original | 1 m 37° C. | 2 m 37° C. | 4 m 37° C. | 1 m 45° C. | 4 m 45° C. | 2 m 60° C. |
| Dextrose Agglomerate & Aspartame | White | Tan | DarkTan | Brown | Brown | Brown | Black/Brown |
| Mannitol Agglomerate & Aspartame | White | White | White | White | White | White | White |
| Dextrose Agglomerate & Aspartame, Sodium | White | Tan | DarkTan | Brown | Brown | Brown | Black/Brown |

TABLE-continued

| Tablet | Original | Stability | | | | | |
|---|---|---|---|---|---|---|---|
| | | 1 m 37° C. | 2 m 37° C. | 4 m 37° C. | 1 m 45° C. | 4 m 45° C. | 2 m 60° C. |
| Bicarbonate & Citric Acid | | | | | | | |
| Mannitol Agglomerate & Aspartame, Sodium Bicarbonate & Citric Acid | White | White | White | White | White | White | White |

As an additional test for formulation stability, the tablets containing both dextrose, citric acid and sodium bicarbonate were chemically analyzed for sodium bicarbonate levels. This chemical analysis for sodium bicarbonate evidenced partial degradation @37° C./4m and @45° C./2m. Full degradation (i.e. none detected) of the sodium bicarbonate was apparent @60° C./2wks.

The tablets containing mannitol, citric acid and sodium bicarbonate were also chemically analyzed for sodium bicarbonate levels. This analysis demonstrated no degradation of the sodium bicarbonate (i.e. no change from original values at all storage conditions).

The above tests clearly show the stability of a high intensity sweetener such as Aspartame in an agglomerate product of the invention.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. An agglomerate particulate intense sweetener composition comprising an alcohol sugar and an intense sweetener wherein the particles have voids therein and a bulk density lower than the alcohol sugar and intense sweetener components.

2. The agglomerate sweetener composition of claim 1 wherein the agglomerate contains a water-soluble binder.

3. The agglomerate sweetener composition of claim 2 wherein the intense sweetener is selected from the group of dipeptides, Acesulfame, Alatame, Steviasides, saccharin and cyclamate.

4. The agglomerate sweetener composition of claim 3 wherein the alcohol sugar is mannitol and the intense sweetener is Aspartame.

5. The agglomerate sweetener composition of claim 1 wherein the alcohol sugar is formed into an agglomerate and the intense sweetener is sorbed on to the agglomerate.

6. The agglomerate sweetener composition of claim 1 wherein the alcohol sugar and the intense sweetener are formed into an agglomerate using a fluidized bed process.

7. The agglomerate sweetener composition of claim 6 wherein a water-soluble binder containing solution is used to form the agglomerate.

8. The agglomerate sweetener composition of claim 7 wherein the water-soluble binder is maltodextrin or the alcohol sugar.

9. The agglomerate sweetener composition of claim 4 wherein a binder is used to form the agglomerate using a fluidized bed process.

10. The agglomerate sweetener composition of claim 9 wherein the binder is maltodextrin or mannitol.

11. The agglomerate sweetener composition of claim 7 wherein the binder solution contains an intense sweetener.

12. The agglomerate sweetener composition of claim 11 wherein the alcohol sugar is mannitol and the intense sweetener is Aspartame.

13. The agglomerate sweetener composition of claim 1 wherein the agglomerate contains an active ingredient.

14. The agglomerate sweetener composition of claim 13 wherein the agglomerate is formed using a fluid bed process.

15. The agglomerate sweetener composition of claim 14 wherein the active ingredient is in the fluid bed.

16. The agglomerate sweetener composition of claim 1 wherein the alcohol sugar is mannitol.

* * * * *

UNITED STATES PATENT AND TRADEMARK OFFICE
CERTIFICATE OF CORRECTION

PATENT NO. : 6,296,868 B1
DATED : October 2, 2001
INVENTOR(S) : William Valentine et al.

It is certified that error appears in the above-identified patent and that said Letters Patent is hereby corrected as shown below:

Column 1,
Line 22, delete "Sand" and substitute therefor -- and --.
Line 27, delete "to-mask" and substitute therefor -- to mask --.
Line 39, delete "alkatine" and substitute therefor -- alkaline --.

Column 2,
Line 5, after "provide" insert -- a --.
Line 51, delete "jn" and substitute therefor -- in --.

Column 3,
Line 15, delete "to;cause" and substitute therefor -- to cause --.
Line 20, delete "absorbed" and substitute therefor -- sorbed --.

Column 4,
Line 63, delete "arntacid" and substitute therefor -- antacid --.

Column 7,
Line 57, delete "owl" and substitute therefor -- bowl --.

Column 12,
Line 57, delete "in)" and substitute therefor -- in --.

Signed and Sealed this

Fourth Day of June, 2002

Attest:

JAMES E. ROGAN
Attesting Officer       Director of the United States Patent and Trademark Office